United States Patent [19]

Shepherd, Jr.

[11] 4,240,985

[45] Dec. 23, 1980

[54] ALDEHYDE SYNTHESIS

[75] Inventor: Lawrence H. Shepherd, Jr., Baton Rouge, La.

[73] Assignee: Ethyl Corporation, Richmond, Va.

[21] Appl. No.: 15,369

[22] Filed: Feb. 26, 1979

[51] Int. Cl.³ .............................................. C07C 47/02
[52] U.S. Cl. ...................................................... 568/483
[58] Field of Search ................................... 260/601 R

[56] References Cited

PUBLICATIONS

Hill et al., Journal of Amer. Chem. Soc., vol. 87, No. 12, (1965) pp. 2772-2773.
Fry et al., Carbonium Ions, vol. 11, ed. Olah et al., Wiley-Intersc. (1970) Chapter 14, pp. 521, 522 and 555-571.

*Primary Examiner*—Werren B. Lone
*Attorney, Agent, or Firm*—Donald L. Johnson; John F. Sieberth

[57] ABSTRACT

Aldehydes are produced by cleaving 2,2-dialkyltetrahydropyrans bearing two hydrogen atoms in the sixth position with a strong acid. The 2,2-dialkyltetrahydropyran can be formed in situ by contacting the strong acid with a primary 6-alken-1-ol having at least one methyl group in the fifth position so that cyclization occurs.

10 Claims, No Drawings

ALDEHYDE SYNTHESIS

This invention relates to the discovery that alkyl substituted alkanals can be produced by cleaving 2,2-dialkyltetrahydropyrans bearing two hydrogen atoms in the sixth position with a strong acid so that a 1,5-hydride shift occurs. It has also been discovered that the 2,2-dialkyltetrahydropyran can be formed in situ by contacting the strong acid with a primary 6-alken-1-ol having at least one methyl group in the fifth position so that cyclization occurs. Thus it is now possible to convert a primary 6-alken-1-ol having at least one methyl group in the fifth position to a methyl substituted alkanal by treating the alkenol with a strong acid under conditions whereby (i) protonation and cyclization, and then (ii) cleavage and a 1,5-hydride shift occur.

So far as is known, the production of aldehydes from an acyclic olefinic alcohol or a tetrahydropyran by means of an intramolecular 1,5-hydride shift has not been reported in the literature heretofore. In J. Am. Chem. Soc. 87, 2772-3 (1965), Hill and Carlson report that heating of 2-deuterio-6-methyl-hept-5-en-2-ol with polyphosphoric acid gave the ketone 6-deuterio-6-methylheptanone-2 in 47 percent yield. In their paper the authors state that the discovery of an intramolecular 1,5-hydride transfer to a simple acyclic carbonium ion implies that this reaction should be much more common than theretofore realized. They indicated they were continuing their studies on the stereochemistry of acid-catalyzed hydride transfer reactions. In spite of their discovery of a ketone synthesis via a 1,5-hydride transfer and despite their indication that further studies in the field would ensue, it appears that neither of the authors (or anyone else for that matter) has previously considered the possibility of producing alkyl substituted alkanals in a cleavage reaction involving an intramolecular 1,5-hydride shift, let alone establishing its feasibility.

Perhaps there is good reason for the lack of a precedent for the process of this invention. Those skilled in the art readily appreciate that the presence, in the Hill and Carlson alkenol, of a methyl group on the hydroxyl-bearing carbon atom would render the deuterium atom of their secondary alkenol quite labile and thus susceptible to the 1,5-hydride shift which they reported in the foregoing paper. In the process of this invention there is no such methyl substitution.

Moreover, in discussing higher-order hydride shifts, Fry and Karabatsos in Volume II of "Carbonium Ions", edited by George A. Olah and Paul von R. Schleyer, Wiley-Interscience, 1970, page 555, state that higher-order shifts might be expected to be more prevalent in systems in which the potential migration origin and terminus are closely constrained, such as in some cyclic systems, rather than in flexible acyclic systems in which there are many possible conformations. It will be appreciated that the process of this invention involves flexible acyclic systems.

Another feature of this invention is that the alkanals are produced in good yield and can be formed in systems containing little, if any, of the corresponding alkanoic acid. As is well known, aldehydes tend to oxidize quite readily so that they are often contaminated with the corresponding acid. But the reaction systems utilized in the practice of this invention make it possible to avoid such carboxylic acid contamination. Further, the process of this invention is very easy to conduct.

Exemplary 2,2-dialkyltetrahydropyrans which may be used in the practice of this invention include 2-isopropyl-2-methyltetrahydropyran, 2-ethyl-2-methyltetrahydropyran, 2-methyl-2-sec-butyltetrahydropyran, 2-methyl-2-(3',3'-dimethylcyclohexyl)tetrahydropyran, 2-methyl-2-tert-butylhydropyran, 2-ethyl-2,4,5-trimethyltetrahydropyran, 2-isopropyl-2,4,5-trimethyltetrahydropyran, 2-tert-butyl-2,4,5-trimethyltetrahydropyran, 2,5-dimethyl-2-tert-butyltetrahydropyran, 2-heptyl-2-methyltetrahydropyran, 2,2-dimethyltetrahydropyran, 2,2-diethyltetrahydropyran, and the like. Similar 2,2-disubstituted tetrahydropyrans such as 2-methyl-2-phenyltetrahydropyran can also be used as reactants in the process. Methods which may be used for preparing such substituted tetrahydropyrans are reported by Crisan in Ann. Chim. (Paris) 13 1, 436-474 (1956), and by Combret et al. in Bull. Soc. Chim. France 1971, No. 10 at pages 3501-8. A particularly desirable method for producing some of the foregoing reactants is set forth in my copending application Ser. No. 15,367, filed Feb. 26, 1979.

Phosphoric acid is the preferred strong acid for use in the process. However, if desired, use may be made of such other acids as polyphosphoric acid, benzene sulfonic acid, toluene sulfonic acid, HCl, $H_2SO_4$, and the like.

The cleavage process is normally conducted at mildly elevated temperatures, e.g., from about 50° C. to about 200° C., and preferably from about 90° C. to about 100° C. Naturally, the system is allowed to interact for a sufficient period for the cleavage to occur. Generally speaking, the reaction can be completed within one or two hours, the length of the reaction period being shorter with higher reaction temperatures. For best results, the strong acid and the 2,2-dialkyltetrahydropyran should be constantly mixed or agitated such as by stirring or shaking. Where it is desired to avoid contamination by oxidation by-products such as carboxylic acids, it is desirable to perform the reaction under an inert atmosphere.

As noted above, the 2,2-dialkyltetrahydropyran can be and preferably is formed in situ by contacting the strong acid with a primary 6-alken-1-ol having at least one methyl group in the fifth position so that cyclization occurs. When there are two methyl groups in the fifth position of the primary 6-alken-1-ol, both a 1,2-methyl shift and cyclization occur.

Exemplary primary 6-alken-1-ols suitable for use in this process include 5-methyl-6-hepten-1-ol, 5,6-dimethyl-6-hepten-1-ol, 5-methyl-6-(4-methyl-3-pentenyl)-6-hepten-1-ol, 5,5,6-trimethyl-6-hepten-1-ol, 2,3,5-trimethyl-6-hepten-1-ol, 2,3,5,6-tetramethyl-6-hepten-1-ol, 2,3,5,5,6-pentamethyl-6-hepten-1-ol, 2,5,5,6-tetramethyl-6-hepten-1-ol, and the like. Suitable procedures for the synthesis of such alkenols are described for example in U.S. Pat. Nos. 3,493,623 and 3,631,065.

The practice of this invention will become still further apparent from a consideration of the ensuing illustrative examples.

EXAMPLE I

5,6,6-trimethylheptanal

A sample of 5,5,6-trimethyl-6-hepten-1-ol (1.76 grams) was treated with 20 milliliters of 85 percent phosphoric acid at steam bath temperature for 1.25 hours with stirring. The product was found to contain, in addition to some 2-methyl-2-tert-tetrahydropyran having a v.p.c. retention temperature of 175° C. on a ¼"×15' Carbowax 20M column, another compound having a retention temperature on this column of 205° C. By means of 2,4-di-nitrophenylhydrazine and NMR it was established that the compound having the retention temperature of 205° C. was 5,6,6-trimethylheptanal. Thus in the process the following gross transformations took place:

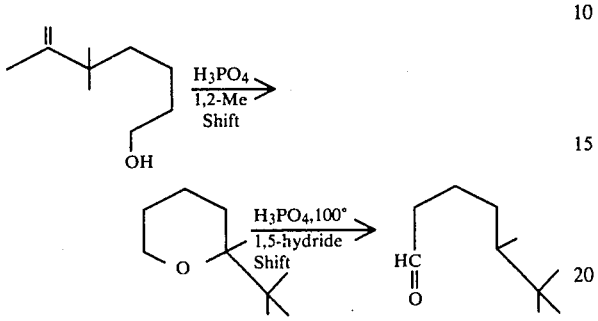

It will be noted that since the initial primary alkenol contained two methyl groups in the fifth position, in addition to protonation and cyclization, a 1,2-methyl migration occurred in the first step of the reaction sequence as depicted. Thus the reaction may be portrayed more specifically as follows:

were noted at 115° C., 165° C., and 230° C. These represented unknown products and impurities.

TABLE

Conversion of 5-methyl-6-hepten-1-ol to 5-methylheptanal

| Reaction Conditions | | Percentages of Components as Determined by Temperature Programmed V.P.C. | | |
|---|---|---|---|---|
| Reaction Temperature | Time, Minutes | 155° C.* | 180° C.* | 225° C.* |
| 75 | 10 | 91% | 6.5% | — |
| 75 | 20 | 77% | 20% | — |
| 90 | 45 | 24% | 22% | — |

*Elution temperature for ¼" × 15' Carbowax 20M column programmed from 80° C.-237° C. at 10°/min.

From the results set forth in the above examples it can be seen that in the process of this invention wherein a primary 6-alken-1-ol is used as the starting material reaction proceeds via (i) protonation at the seventh position; (ii) formation of a tertiary carbonium ion in the fifth position either via a 1,2-hydride shift (if the initial alkenol contains only one methyl group in the fifth position) or a 1,2-methyl shift (if the initial alkenol contains two methyl groups in the fifth position); (iii) intramolecular ring closure and proton elimination involving the oxygen atom and the tertiary carbonium ion so formed that a 2,2-dialkyltetrahydropyran is formed; and (iv) cleavage coupled with an intramolecular 1,5-

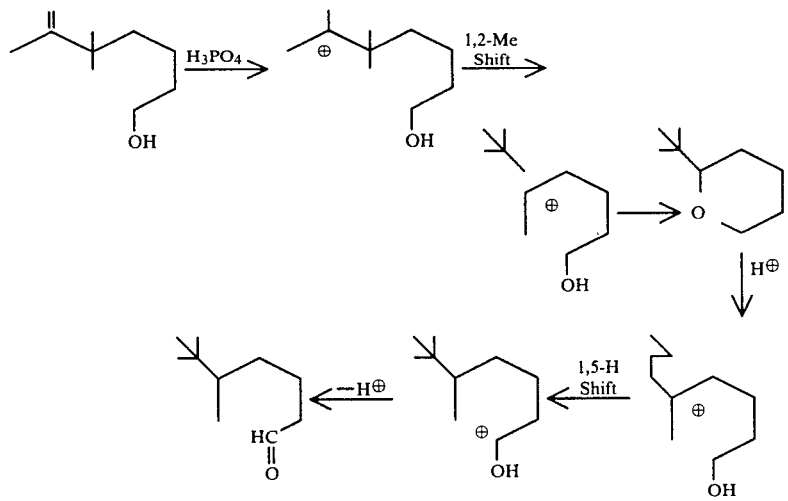

EXAMPLE II 5-methylheptanal

Several experiments were conducted in which 5-methyl-6-hepten-1-ol was treated with 85 percent phosphoric acid under different reaction conditions. Each reaction was followed by vapor phase chromatography (v.p.c.). In each case, after the specified reaction time the mixtures were dissolved in cold diethyl ether, washed with water, aqueous sodium bicarbonate and water again, dried over anhydrous magnesium sulfate and then injected into a v.p.c. Reaction conditions and results of the experiments are set forth in the ensuing table. The unchanged alkenol peak occurred at 225° C. and the peak at 155° C. represented the intermediate product, 2-ethyl-2-methyltetrahydropyran. The peak at 180° C. represents 5-methylheptanal formed by means of the intramolecular 1,5-hydride shift. Other peaks hydride shift so that an aldehyde is formed, the foregoing positions in the alkenol being relative to the carbon atom carrying the hydroxyl group.

The methyl-branched aldehydes producible by the process of this invention undergo the well-known reactions characteristic of their corresponding straight chain isomers. Thus they can be used in the synthesis of a variety of end products, such as acids, alcohols, oximes, hydrazones, semicarbazones, and the like. In purified form such aldehydes can be used as uniform substrates for testing the efficacy of antioxidants. In addition, the aldehydes producible by the process of this invention have utility in the field of perfumery by virtue of their characteristic fragrance properties.

I claim:

1. A process of producing an alkyl-substituted alkanal which comprises contacting a 2,2-di-lower-alkyl tetrahydropyran bearing two hydrogen atoms in the sixth position with a strong acid selected from the group consisting of phosphoric acid, polyphosphoric acid, benzene sulfonic acid, toluene sulfonic acid, hydrochloric acid, and sulphuric acid at a temperature within the range of about 50° C. to about 200° C. at which said 2,2-di-lower-alkyl tetrahydropyran is cleaved and a 1,5-hydride shift occurs so that an alkyl-substituted alkanal is produced.

2. A process according to claim 1 wherein said strong acid is phosphoric acid.

3. A process according to claim 1 wherein said 2,2-di-lower-alkyl tetrahydropyran is formed in situ by contacting said strong acid with a primary 6-alken-1-ol having one methyl group and one hydrogen atom in the fifth position so that a 2,2-di-lower-alkyl tetrahydropyran is formed via (i) protonation in the seventh position, (ii) formation of a tertiary carbonium ion in the fifth position via a 1,2-hydride shift and (iii) intramolecular ring closure and proton elimination involving the oxygen atom and the tertiary carbonium ion.

4. A process according to claim 1 wherein said 2,2-di-lower-alkyl tetrahydropyran is formed in situ by contacting said strong acid with a primary 6-alken-1-ol having two methyl groups in the fifth position so that a 2,2-di-lower-alkyl tetrahydropyran is formed via (i) protonation in the seventh position, (ii) formation of a tertiary carbonium ion in the fifth position via a 1,2-methyl shift and (iii) intramolecular ring closure and proton elimination involving the oxygen atom and the tertiary carbonium ion.

5. A process according to claim 3 wherein said acid is phosphoric acid.

6. A process according to claim 4 wherein said acid is phosphoric acid.

7. A process according to claim 2 performed at a temperature of about 90° to about 100° C.

8. A process according to claim 2 performed at a temperature of at least about 90° C.

9. A process according to claim 3 wherein said 6-alken-1-ol is 5-methyl-6-hepten-1-ol so that said 2,2-dialkyltetrahydropyran is 2-ethyl-2-methyltetrahydropyran and said alkanal is 5-methylheptanal.

10. A process according to claim 4 wherein said 6-alken-1-ol is 5,5,6-trimethyl-6-hepten-1-ol so that said 2,2-dialkyltetrahydropyran is 2-methyl-2-tert-butyl-tetrahydropyran and said alkanal is 5,6,6-trimethylheptanal.

* * * * *

UNITED STATES PATENT AND TRADEMARK OFFICE
CERTIFICATE OF CORRECTION

PATENT NO. : 4,240,985
DATED : December 23, 1980
INVENTOR(S) : Lawrence H. Shepherd, Jr.

It is certified that error appears in the above-identified patent and that said Letters Patent are hereby corrected as shown below:

The chemical equations between lines 28 and 52 of columns 3 and 4 should read:

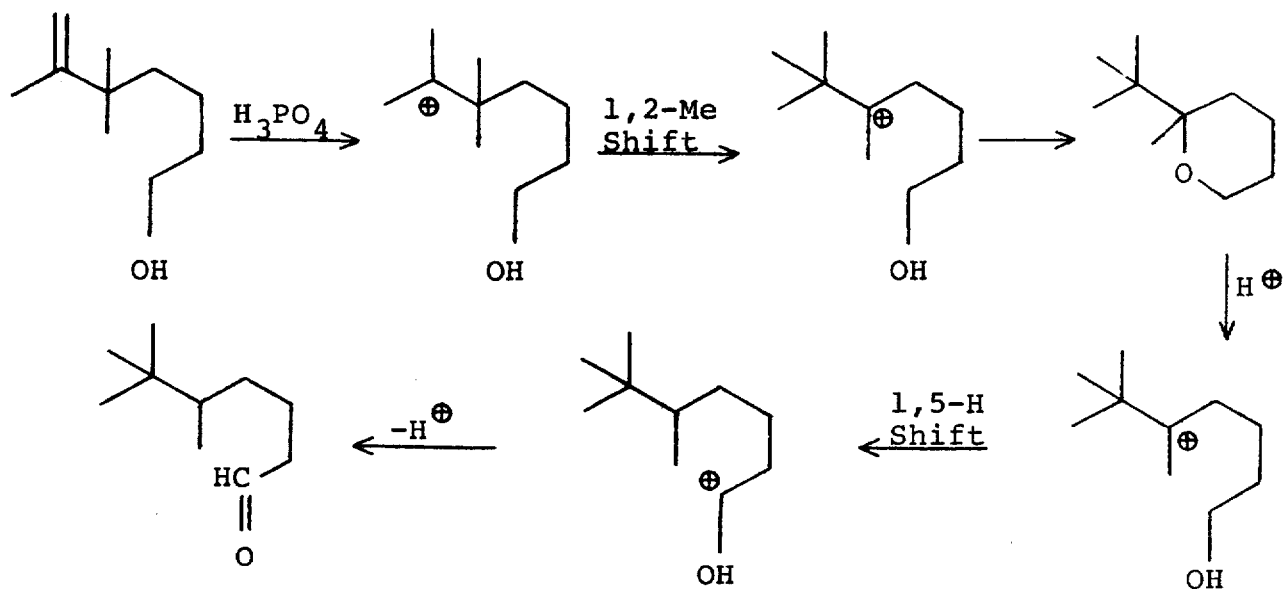

Signed and Sealed this

Twenty-eighth Day of April 1981

[SEAL]

Attest:

RENE D. TEGTMEYER

*Attesting Officer*  *Acting Commissioner of Patents and Trademarks*